(12) United States Patent
Morrell et al.

(10) Patent No.: US 7,738,099 B2
(45) Date of Patent: Jun. 15, 2010

(54) PATHOGEN AND PARTICLE DETECTOR SYSTEM AND METHOD

(75) Inventors: Michael Morrell, Tucson, AZ (US); Jian-Ping Jiang, Tucson, AZ (US)

(73) Assignee: Biovigilant Systems, Inc., Tucson, AZ (US)

( * ) Notice: Subject to any disclaimer, the term of this patent is extended or adjusted under 35 U.S.C. 154(b) by 547 days.

(21) Appl. No.: 11/457,988

(22) Filed: Jul. 17, 2006

(65) Prior Publication Data

US 2010/0108910 A1 May 6, 2010

Related U.S. Application Data

(60) Provisional application No. 60/700,008, filed on Jul. 15, 2005.

(51) Int. Cl.
*G01N 15/02* (2006.01)
(52) U.S. Cl. .................. 356/336; 356/369; 356/335; 356/343
(58) Field of Classification Search .......... 356/369, 356/335–343
See application file for complete search history.

(56) References Cited

U.S. PATENT DOCUMENTS

| | | | |
|---|---|---|---|
| 3,457,407 A | 7/1969 | Goldberg | 250/373 |
| 3,845,480 A | 10/1972 | Steinberg | 340/236 |
| 3,710,933 A | 1/1973 | Fulwyler et al. | 203/3.1 |
| 3,826,364 A | 7/1974 | Bonner et al. | 209/3.1 |
| 3,850,525 A | 11/1974 | Kaye | 356/73 |
| 3,867,640 A | 2/1975 | Paulsen | 250/573 |
| 4,175,865 A | 11/1979 | Horvath et al. | 356/338 |
| 4,226,533 A | 10/1980 | Snowman et al. | 356/338 |
| 4,251,733 A * | 2/1981 | Hirleman, Jr. | 356/335 |
| 4,286,876 A | 9/1981 | Hogg et al. | 356/343 |
| 4,348,111 A | 9/1982 | Goulas et al. | 356/336 |
| 4,355,897 A | 10/1982 | Kaye | 356/338 |

(Continued)

FOREIGN PATENT DOCUMENTS

EP      0 214 769      8/1986

(Continued)

OTHER PUBLICATIONS

Inglesby et al., "Anthrax as a Biological Weapon", JAMA, May 12, 1999, vol. 281, No. 18, pp. 1735-1745 & published correction dated Apr. 19, 2000, vol. 283, No. 15, p. 1963.

(Continued)

*Primary Examiner*—Gregory J Toatley, Jr.
*Assistant Examiner*—Iyabo S Alli
(74) *Attorney, Agent, or Firm*—Quarles & Brady LLP (57) ABSTRACT

The system includes an excitation source for providing a beam of electromagnetic radiation having a source wavelength. A first wavelength selective device is positioned to be impinged by the beam of electromagnetic radiation. The first wavelength selective device is constructed to transmit at least a portion of any radiation having the source wavelength and to reflect radiation of other wavelengths. A medium containing particles is positioned to be impinged by the beam of electromagnetic radiation. At least a portion of the beam of electromagnetic radiation becomes scattered within the medium, the scattered electromagnetic radiation including forward scattered electromagnetic radiation and backward scattered electromagnetic radiation. An optical detector is positioned to receive backward and/or forward scattered electromagnetic radiation.

32 Claims, 9 Drawing Sheets

U.S. PATENT DOCUMENTS

| | | | |
|---|---|---|---|
| 4,583,859 A | 4/1986 | Hall, II | 356/438 |
| 4,599,307 A | 7/1986 | Saunders et al. | 435/34 |
| 4,727,020 A | 2/1988 | Recktenwald | 435/6 |
| 4,728,190 A | 3/1988 | Knollenberg | 356/336 |
| 4,737,648 A | 4/1988 | Smith et al. | 250/560 |
| 4,830,494 A | 5/1989 | Ishikawa et al. | 356/336 |
| 4,839,529 A | 6/1989 | Fruengel | 250/574 |
| 4,940,326 A | 7/1990 | Tatsuno | 356/336 |
| 5,006,986 A | 4/1991 | Inoue | 364/413 |
| 5,056,918 A | 10/1991 | Bott et al. | 356/336 |
| 5,083,865 A | 1/1992 | Kinney et al. | 356/338 |
| 5,085,500 A | 2/1992 | Blesener | 356/338 |
| 5,101,113 A | 3/1992 | Hirleman, Jr. et al. | 250/574 |
| 5,117,357 A | 5/1992 | Inoue | 364/413 |
| 5,121,988 A | 6/1992 | Blesener et al. | 356/442 |
| 5,123,731 A | 6/1992 | Yoshinaga et al. | 356/73 |
| 5,125,737 A | 6/1992 | Rodriguez et al. | 356/39 |
| 5,132,548 A | 7/1992 | Borden et al. | 250/574 |
| 5,166,537 A | 11/1992 | Horiuchi et al. | 250/573 |
| 5,180,065 A | 1/1993 | Touge et al. | 209/577 |
| 5,231,378 A | 7/1993 | Dennis et al. | 340/630 |
| 5,257,087 A | 10/1993 | Furuya | 356/336 |
| 5,266,798 A | 11/1993 | Borden et al. | 250/239 |
| 5,286,452 A | 2/1994 | Hansen | 422/73 |
| 5,305,072 A | 4/1994 | Sawada et al. | 356/336 |
| 5,315,115 A | 5/1994 | Gerber | 250/338 |
| 5,366,858 A | 11/1994 | Koizumi et al. | 435/5 |
| 5,383,024 A | 1/1995 | Maxey et al. | 356/336 |
| 5,408,307 A | 4/1995 | Yamamoto et al. | 356/73 |
| 5,416,580 A | 5/1995 | Trainer | 356/336 |
| 5,426,501 A * | 6/1995 | Hokanson et al. | 356/335 |
| 5,428,964 A | 7/1995 | Lobdell | 62/176 |
| 5,448,364 A | 9/1995 | Moran | 356/430 |
| 5,456,102 A | 10/1995 | Moorehead | 73/3 |
| 5,457,526 A | 10/1995 | Kosaka | 356/72 |
| 5,467,189 A | 11/1995 | Kreikebaum et al. | 356/336 |
| 5,469,251 A | 11/1995 | Kosaka et al. | 356/73 |
| 5,481,357 A | 1/1996 | Ahsan et al. | 356/338 |
| 5,506,673 A | 4/1996 | Kosaka et al. | 356/72 |
| 5,561,515 A | 10/1996 | Hairston et al. | 356/28 |
| 5,600,438 A | 2/1997 | Kreikebaum et al. | 356/339 |
| 5,646,597 A | 7/1997 | Hamburger et al. | 340/627 |
| 5,684,585 A | 11/1997 | Girvin | 356/336 |
| 5,701,012 A | 12/1997 | Ho | 250/461.2 |
| 5,760,900 A | 6/1998 | Ito et al. | 356/338 |
| 5,864,399 A | 1/1999 | Girvin et al. | 356/339 |
| 5,895,922 A | 4/1999 | Ho | 250/491.2 |
| 5,946,093 A | 8/1999 | DeFreez et al. | 356/339 |
| 5,969,622 A | 10/1999 | Hamburger et al. | 340/627 |
| 5,986,555 A | 11/1999 | Hamburger et al. | 340/627 |
| 5,995,686 A | 11/1999 | Hamburger et al. | 385/12 |
| 6,008,729 A | 12/1999 | Hamburger et al. | 340/627 |
| 6,087,947 A * | 7/2000 | Hamburger et al. | 356/438 |
| 6,312,914 B1 | 11/2001 | Kardos et al. | 435/6 |
| 6,386,015 B1 | 5/2002 | Rader et al. | 73/31 |
| 6,537,829 B1 | 3/2003 | Zarling et al. | 436/514 |
| 6,819,411 B1 | 11/2004 | Sharpe et al. | 356/72 |
| 6,831,279 B2 | 12/2004 | Ho | 250/468.1 |
| 6,972,424 B1 | 12/2005 | Quist et al. | 250/573 |
| 7,053,783 B2 | 5/2006 | Hamburger et al. | 340/630 |
| 7,106,442 B2 | 9/2006 | Silcott et al. | 356/336 |
| 7,430,046 B2 * | 9/2008 | Jiang et al. | 356/443 |
| 7,471,393 B2 * | 12/2008 | Trainer | 356/336 |
| 2001/0012429 A1 | 8/2001 | Wach et al. | 385/115 |
| 2001/0024800 A1 | 9/2001 | Garcia-Rubio et al. | 435/7.21 |
| 2002/0028519 A1 | 3/2002 | Yguerabide et al. | 436/518 |
| 2002/0032165 A1 | 3/2002 | Johnson et al. | 514/44 |
| 2002/0045276 A1 | 4/2002 | Yguerabide et al. | 436/518 |
| 2002/0046966 A1 | 4/2002 | Muscate-Magnussen | 210/198.2 |
| 2002/0065468 A1 | 5/2002 | Utzinger et al. | 600/476 |
| 2002/0103517 A1 | 8/2002 | West et al. | 607/88 |
| 2002/0119486 A1 | 8/2002 | Oberhardt | 435/6 |
| 2002/0132766 A1 | 9/2002 | DeGrado et al. | 514/12 |
| 2002/0135752 A1 | 9/2002 | Sokolov et al. | 356/39 |
| 2002/0143243 A1 | 10/2002 | Georgakoudi et al. | 600/310 |
| 2002/0165456 A1 | 11/2002 | Canpolat et al. | 600/473 |
| 2002/0171831 A1 | 11/2002 | Backman et al. | 356/369 |
| 2003/0013973 A1 | 1/2003 | Georgakoudi et al. | 600/473 |
| 2003/0022249 A1 | 1/2003 | Schmitz et al. | 435/7.21 |
| 2003/0030783 A1 | 2/2003 | Roche et al. | 356/39 |
| 2003/0052281 A1 | 3/2003 | Rader et al. | 250/461.1 |
| 2003/0077627 A1 | 4/2003 | Worthington et al. | 435/6 |
| 2003/0093092 A1 | 5/2003 | West et al. | 606/139 |
| 2003/0096302 A1 | 5/2003 | Yguerabide et al. | 435/7.1 |
| 2003/0098421 A1 | 5/2003 | Ho | 250/458.1 |
| 2003/0098422 A1 | 5/2003 | Silcott et al. | 250/458.1 |
| 2003/0124733 A1 | 7/2003 | Bushway et al. | 436/174 |
| 2003/0137669 A1 | 7/2003 | Rollins et al. | 356/479 |
| 2003/0139886 A1 | 7/2003 | Bodzin et al. | 702/28 |
| 2003/0157731 A1 | 8/2003 | Yguerabide et al. | 436/523 |
| 2003/0157732 A1 | 8/2003 | Baker et al. | 436/531 |
| 2003/0159498 A1 | 8/2003 | Small | 73/24.02 |
| 2003/0207328 A1 | 11/2003 | Yguerabide et al. | 435/7.1 |
| 2003/0223063 A1 * | 12/2003 | Hill et al. | 356/340 |
| 2003/0228682 A1 | 12/2003 | Lakowicz et al. | 435/287.2 |
| 2003/0231309 A1 | 12/2003 | Fulghum, Jr. et al. | 356/338 |
| 2003/0232445 A1 | 12/2003 | Fulghum, Jr. | 436/63 |
| 2004/0009941 A1 | 1/2004 | Johnson et al. | 514/44 |
| 2004/0021861 A1 | 2/2004 | Lewis et al. | 356/326 |
| 2004/0023317 A1 | 2/2004 | Motamedi et al. | 435/14 |
| 2004/0038413 A1 | 2/2004 | Kramer | 436/63 |
| 2004/0057050 A1 | 3/2004 | Beck et al. | 356/336 |
| 2004/0072356 A1 | 4/2004 | Senisterra et al. | 436/63 |
| 2004/0073120 A1 | 4/2004 | Motz et al. | 600/478 |
| 2004/0079893 A1 | 4/2004 | Dietz et al. | 250/458.1 |
| 2004/0159799 A1 | 8/2004 | Saccomanno | 250/461.1 |
| 2004/0161143 A1 | 8/2004 | Dietz et al. | 382/133 |
| 2004/0174821 A1 | 9/2004 | Eggeling et al. | 370/252 |
| 2004/0197232 A1 | 10/2004 | Kramer | 422/73 |
| 2004/0218184 A1 | 11/2004 | Jorgenson et al. | 356/419 |
| 2005/0019842 A1 | 1/2005 | Prober et al. | 435/7.9 |
| 2005/0020922 A1 | 1/2005 | Frangioni et al. | 600/473 |
| 2005/0020923 A1 | 1/2005 | Frangioni et al. | 600/473 |
| 2005/0026831 A1 | 2/2005 | Bodmer et al. | 514/12 |
| 2005/0057749 A1 | 3/2005 | Dietz et al. | 356/318 |
| 2005/0073683 A1 | 4/2005 | Gard et al. | 356/337 |
| 2005/0079526 A1 | 4/2005 | Senisterra et al. | 435/6 |
| 2005/0105077 A1 | 5/2005 | Padmanabhan et al. | 356/39 |
| 2005/0112784 A1 | 5/2005 | Yguerabide et al. | 436/518 |
| 2005/0119541 A1 | 6/2005 | Lorenz et al. | 600/316 |
| 2005/0130324 A1 | 6/2005 | West et al. | 436/523 |
| 2005/0137130 A1 | 6/2005 | Bodmer et al. | 514/12 |
| 2005/0141843 A1 | 6/2005 | Warden et al. | 385/141 |
| 2005/0147533 A1 | 7/2005 | Cole et al. | 422/73 |
| 2005/0172852 A1 | 8/2005 | Anderson et al. | 106/31.03 |
| 2005/0194546 A1 | 9/2005 | Saccomanno | 250/461.1 |
| 2005/0220886 A1 | 10/2005 | Bodmer et al. | 424/489 |
| 2005/0240107 A1 | 10/2005 | Alfano et al. | 600/476 |
| 2005/0243307 A1 | 11/2005 | Silcott et al. | 356/73 |
| 2005/0243314 A1 | 11/2005 | Chinnock | 356/364 |

FOREIGN PATENT DOCUMENTS

| | | |
|---|---|---|
| EP | 0 463 795 | 6/1991 |
| EP | 0 618 440 | 3/1994 |
| EP | 0 737 307 | 6/1994 |
| EP | 0 435 166 | 10/1995 |
| EP | 0 711 991 | 5/1996 |
| EP | 0 595 290 | 7/1997 |
| EP | 0 475 748 | 11/1997 |
| EP | 1 158 292 | 11/2001 |
| GB | 1 298 658 | 1/1970 |
| GB | 2 044 445 | 1/1980 |
| JP | 02-165033 | 6/1990 |

| | | |
|---|---|---|
| JP | 03-108635 | 5/1991 |
| JP | 04-185654 | 7/1992 |
| WO | WO 90/10282 | 9/1990 |
| WO | WO 91/10123 | 7/1991 |
| WO | WO 93/16368 | 8/1993 |
| WO | WO 95/09354 | 4/1995 |
| WO | WO 98/34094 | 6/1998 |

OTHER PUBLICATIONS

Pan et al., "Backward-enhanced fluorescence from clusters of microspheres and particles of tryptophan", Applied Optics, vol. 41, No. 15, May 20, 2002, pp. 2994-2999.

Veselovskii et al., "Angle- and size-dependent characteristics of incoherent Raman and fluorescent scattering by microspheres", Applied Optics, Sep. 20, 2002, vol. 41, No. 27, pp. 5783-5791.

Jeys et al., "Bio-Aerosol Fluorescence Sensor", Proc. IRIS Active Systems, 1998, vol. 1, pp. 235-249.

Met One Instruments, Inc., Product Overviews/Brochures, Particle Counters, www.metone.com.

Terra Universal Corp., Product Overviews/Brochures, Particle Counters, www.terrauniversal.com.

Particle Measuring Systems, Inc., Airborne Particle Counters, List of Products, www.pmeasuring.com.

"Continuous Rapid Biological Aerosol Detection with the Use of Fluorescence: Outdoor Test Results" Eversole et al., Field Analytical Chemistry and Technology 3(4-5):24-259,1999.

"Bio-Aerosol Flurorescence Sensor" Jeys et al., Proc. IRIS Active Systems, 1998, vol. 1, p. 235-249.

"Simslin II-A Portable Airborne Dust Measuring Instrument Employing a Light Scattering Technique" Casswell et al., Conference Proceedings of the Fourth WVU Conference on Coal Mine Electroenergy, 1978, pp. 20-1 to 21-1.

"Instrumentation Airborne Particle Counters-IPS Series" Clean Room Products, Inc., pp. H1-H4.

Met One Model 228 and 229 Particle Concentration Meter and Particle Counter, Date Unknown, prior to 1996 APC Airborne Particle Counter Model P3610 Article, Bioset, 2002.

* cited by examiner

PATHOGEN AND PARTICLE DETECTOR SYSTEM AND METHOD

CROSS-REFERENCE TO RELATED APPLICATION

This application claims priority to copending U.S. Provisional Application entitled, "Pathogen and Particle Detector System and Method," having Ser. No. 60/700,008, filed Jul. 15, 2005, the contents of which are entirely incorporated herein by reference.

FIELD OF THE INVENTION

The present invention relates generally to a system and method for detecting airborne or waterborne particles, and more particularly to a system and method for detecting airborne or waterborne particles and classifying the detected particles by size. The invention has particular utility in detecting and classifying by size allergens and biological warfare agents and will be described in connection with such utility, although other utilities are contemplated.

BACKGROUND OF THE INVENTION

An urban terrorist attack involving release of biological warfare agents such as *bacillus anthracis* (anthrax) is presently a realistic concern. Weaponized anthrax spores are extremely dangerous because they can gain passage into the human lungs. A lethal inhalation dose of anthrax spores for humans, $LD_{50}$ (lethal dose sufficient to kill 50% of the persons exposed) is estimated to be 2,500 to 50,000 spores (see T. V. Inglesby, et al., "Anthrax as a Biological Weapon", JAMA, vol. 281, page 1735, 1999). Some other potential weaponized bio-agents are *yersinia pestis* (plague), *clostidium botulinum* (botulism), and *francisella tularensis*. In view of this potential threat, there is currently a need for an early warning system to detect such an attack.

Laser particle counters are known in which a laser beam is directed through a sample and the light, which travels through the sample, is detected and analyzed to detect scattered light from particles in the sample. One problem with existing detectors or particle counters which, are designed for detection of scattered light is that the scattering signal must be extracted from the incident illumination light source signal. This involves detecting a weak signal (scattering from small particles) from a very noisy background (glare from the laser source). This feature has long caused major difficulty in the instrumentation of laser particle counters. Conventionally designed laser particle counters employ costly and elaborate means to reduce the glare from the laser illumination source and to measure particle scattering against a large background noise, rendering the counters fragile and expensive. Currently, conventionally designed laser particle counters are fragile and expensive, and unsuited to this application. The conventional techniques used for laser particle counting include the laser Doppler method, which measures the speed of the particle and deduces size information, the transient time method which measures the time needed for particles to traverse a sensing region, and large angle multi-sensor design, which is capable of measuring only small particles. A proposed bio-sensor based on laser-induced fluorescence using a pulsed UV laser is described by T. H. Jeys, et al., Proc. IRIS Active Systems, vol. 1, p. 235, 1998. This is capable of detecting an aerosol concentration of five particles per liter of air, but involves expensive and delicate instruments. Other particle counters are manufactured by Met One Instrument, Inc, of Grants Pass, Oreg., Particle Measurement Systems, Inc., of Boulder, Colo., and Terra Universal Corp., of Anaheim, Calif. By virtue of their design, these particle counter configurations require precision optical alignment, as well as sophisticated sensors and electronics. These products are geared towards laboratory use and cost thousands of dollars for a single unit. Thus, they are not suitable for a field-deployed detector, nor are they designed specifically for detection of biological warfare agents.

Various detectors have been designed to detect fluid borne allergen particles and provide warning to sensitive individuals when the number of particles within an air sample exceeds a predetermined minimum value. These are described in U.S. Pat. Nos. 5,646,597, 5,969,622, 5,986,555, 6,008,729, and 6,087,947, all to Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmitted light. An alarm is actuated if the light detected at the detector is above a predetermined level. Although these devices are sufficient for the purpose of providing an alarm indication based on the presence of allergen particles, they are not suitable for field deployment and do not meet the more stringent requirements for a pathogen detector for detecting biological warfare agents.

SUMMARY OF THE INVENTION

The present invention provides an improvement over prior art systems and methods for pathogen and particle detection. More particularly, a novel fluorescence signal collection scheme was developed to fully utilize the unique angular distribution pattern of in-elastic scattering intensity, i.e., the fluorescence from a particle. It has been demonstrated both theoretically and experimentally that in-elastic scattering by particles has preferential intensity angular distributions in backward (strongest) and forward (second strongest) directions [Ref. 1 "Backward-enhanced fluorescence from clusters of microspheres and particles of tryptophan" Yong-Le Pan et al., Appl. Opt. Vol. 41, 2994, 2002; Ref. 2 "Angle- and size-dependent characteristics of incoherent Raman and fluorescent scattering by microspheres" Igor Veselovskii et al., Appl. Opt. Vol. 41, 5783, 2002]. Briefly described, in one embodiment the system includes an excitation source for providing a beam of electromagnetic radiation having a source wavelength. A first wavelength selective device such as a dichroic beamsplitter is positioned to be impinged by the beam of electromagnetic radiation. The first wavelength selective device is constructed to transmit at least a portion of any radiation having the source wavelength and to reflect radiation of other wavelengths. A medium containing particles is positioned to be impinged by the beam of electromagnetic radiation. At least a portion of the beam of electromagnetic radiation becomes scattered within the medium, the scattered electromagnetic radiation including forward scattered electromagnetic radiation and backward scattered electromagnetic radiation. An optical detector or detectors is/are positioned to collect forward and backward scattered electromagnetic radiation.

The present invention can also be viewed as providing methods for pathogen and particle detection. In this regard, one embodiment of such a method, among others, can be broadly summarized by the following steps: emitting a beam of electromagnetic radiation; transmitting at least a portion of the beam of electromagnetic radiation through a first wavelength selective device; impinging a medium containing particles with the portion of the beam of electromagnetic radiation, wherein the particles scatter the electromagnetic radiation in a forward direction and in a backward direction; reflecting at least a portion of the backward scattered electromagnetic radiation with the first wavelength selective device; and collecting at least a portion of the forward and backward scattered electromagnetic radiation at a first optical detector, whereby the particles that scattered the electromagnetic radiation in the forward and backward direction are sized.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE INVENTION

Figure 1:
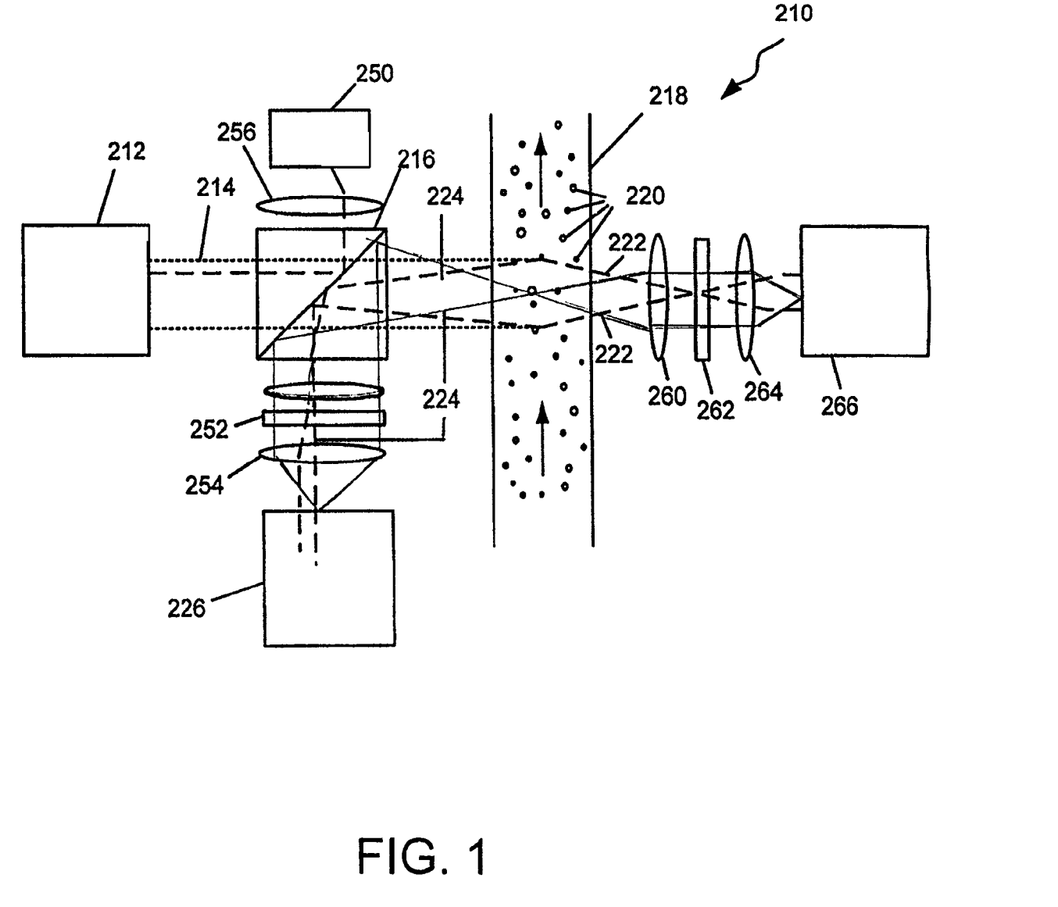
FIG. 1 is a representation of an optical system for a fluid particle detector system according to a first exemplary embodiment of the invention.

FIG. 1 is a representation of an optical system for a fluid particle detector system according to a first exemplary embodiment of the invention. This first exemplary embodiment of the system is particularly directed to detect airborne or waterborne bio-terrorist agents deliberately released by terrorists or others, but may also be used in civilian applications to detect harmful levels of other airborne or waterborne particles which may exist naturally such as mold or bacteria, or which may have been accidentally, inadvertently, naturally, or deliberately released, or other industrial applications such as the food and manufacturing industries, as well as clean room applications.

The term "fluid borne particles" as used herein means both airborne particles and waterborne particles.

The term "pathogen" as used herein refers to any airborne or waterborne particles, biological agent, or toxin, which could potentially harm or even kill humans exposed to such particles if present in the air or water in sufficient quantities. As used herein, "biological agent" is defined as any microorganism, pathogen, or infectious substance, toxin, biological toxin, or any naturally occurring, bioengineered or synthesized component of any such micro-organism, pathogen or infectious substance, whatever its origin or method of production. Such biological agents include, for example, biological toxins, bacteria, viruses, rickettsiae, spores, fungi, and protozoa, as well as others known in the art.

"Biological toxins" are poisonous substances produced or derived from living plants, animals, or microorganisms, but also can be produced or altered by chemical means. A toxin, however, generally develops naturally in a host organism (i.e., saxitoxin is produced by marine algae), but genetically altered and/or synthetically manufactured toxins have been produced in a laboratory environment. Compared with microorganisms, toxins have a relatively simple biochemical composition and are not able to reproduce themselves. In many aspects, they are comparable to chemical agents. Such biological toxins are, for example, botulinum and tetanus toxins, staphylococcal enterotoxin B, tricothecene mycotoxins, ricin, saxitoxin, Shiga and Shiga-like toxins, dendrotoxins, erabutoxin b, as well as other known toxins.

The detector system is designed to detect airborne or waterborne particles and produce outputs indicating, for instance, the number of particles of each size within the range, which is detected in a sample, and indicate whether the particles are biologic or non-biologic. The system may also produce an alarm signal or other response if the number of particles exceeds a predetermined value above a normal background level, and/or are biological organisms or biological agents and potentially dangerous.

FIG. 1 is a representation of an optical system 210 for a fluid particle detector system according to a first exemplary embodiment of the invention. As shown in FIG. 1, the optical system 210 includes an excitation source 212 providing a beam of electromagnetic radiation 214 having a source wavelength. A first wavelength selective device 216, which in one embodiment comprises a dichroic beamsplitter is positioned to be impinged by the beam of electromagnetic radiation 214. The first wavelength selective device 216 is constructed to transmit at least a portion of any radiation having the source wavelength and to reflect radiation of other wavelengths. The first wavelength selective device 216 may operate to reflect potential spurious spectral emissions from the excitation source 212. A portion of the beam of electromagnetic radiation 214 may be reflected by the first wavelength selective device 216 toward a power monitor detector 250. The power monitor detector 250 may operate in communication with the excitation source 212 and, optionally, operate as a part of a feedback loop that maintains constant output power from the excitation source 212. The portion of the beam of electromagnetic radiation 214 reflected by the first wavelength selective device 216 toward the power monitor detector 250 may be focused by a power monitor lens 256.

A medium 218 containing particles 220 is positioned to be impinged by the beam of electromagnetic radiation 214. At least a portion of the beam of electromagnetic radiation 214 becomes scattered electromagnetic radiation within the medium 218. The scattered electromagnetic radiation includes forward scattered electromagnetic radiation 222 and backward scattered electromagnetic radiation 224. A first optical detector 226 is positioned to receive backward scattered electromagnetic radiation 224. The backward scattered electromagnetic radiation 224 may be reflected by the first wavelength selective device 216 toward the optical detector 226. A band pass filter 252 may be utilized between the first wavelength selective device 216 and the optical detector 226 to minimize any back scattered light from the beam of electromagnetic radiation 214 and/or to select out specific portions of the spectrum to be measured. A focusing lens 254 may be utilized between the first wavelength selective device 216 and the optical detector 226 to focus the backward scattered electromagnetic radiation 224 toward the optical detector 226.

As shown in FIG. 1, the forward scattered electromagnetic radiation 222 may be directed to impinge a first beam blocker lens 260. The first beam blocker lens 260 may be designed to reflect non-scattered elements of the beam of electromagnetic radiation 214, which may prevents glare on optical detectors. The first beam blocker lens 260 may have a material, such as vinyl, attached to a front surface to reflect the non-scattered elements of the beam of electromagnetic radiation 214. Additional possible considerations for the first beam blocker lens 260 are disclosed in patent application Ser. No. 11/193,204, incorporated herein by reference.

The forward scattered electromagnetic radiation may then be directed to a first optic element 262, which is a low pass filter, or similar wavelength selective element, in the third exemplary embodiment. The first optic element 262 may allow at least a portion of the forward scattered electromagnetic radiation 222 and reflect a portion of the forward scattered electromagnetic radiation 222. More specifically, the first optic element 262 may reflect a fluorescence signal portion of the forward scattered electromagnetic radiation 222, while allowing a remainder of the forward scattered electromagnetic radiation 222 to be transmitted through. A second beam blocker lens 264 may focus the transmitted portion of the forward scattered electromagnetic radiation 222 toward a particle detector 266. The particle detector 266 may, for instance, be a photodiode for sizing the particles 220.

The reflected fluorescence signal portion of the forward scattered electromagnetic radiation 222 may be directed back through the medium 218 to be reflected by the first wavelength selective device 216 toward the optical detector 226. The focusing lens 254 may be utilized between the first wavelength selective device 216 and the optical detector 226 to focus the reflected fluorescence signal portion of the forward scattered electromagnetic radiation 222 toward the optical detector 226.

Figure 2:
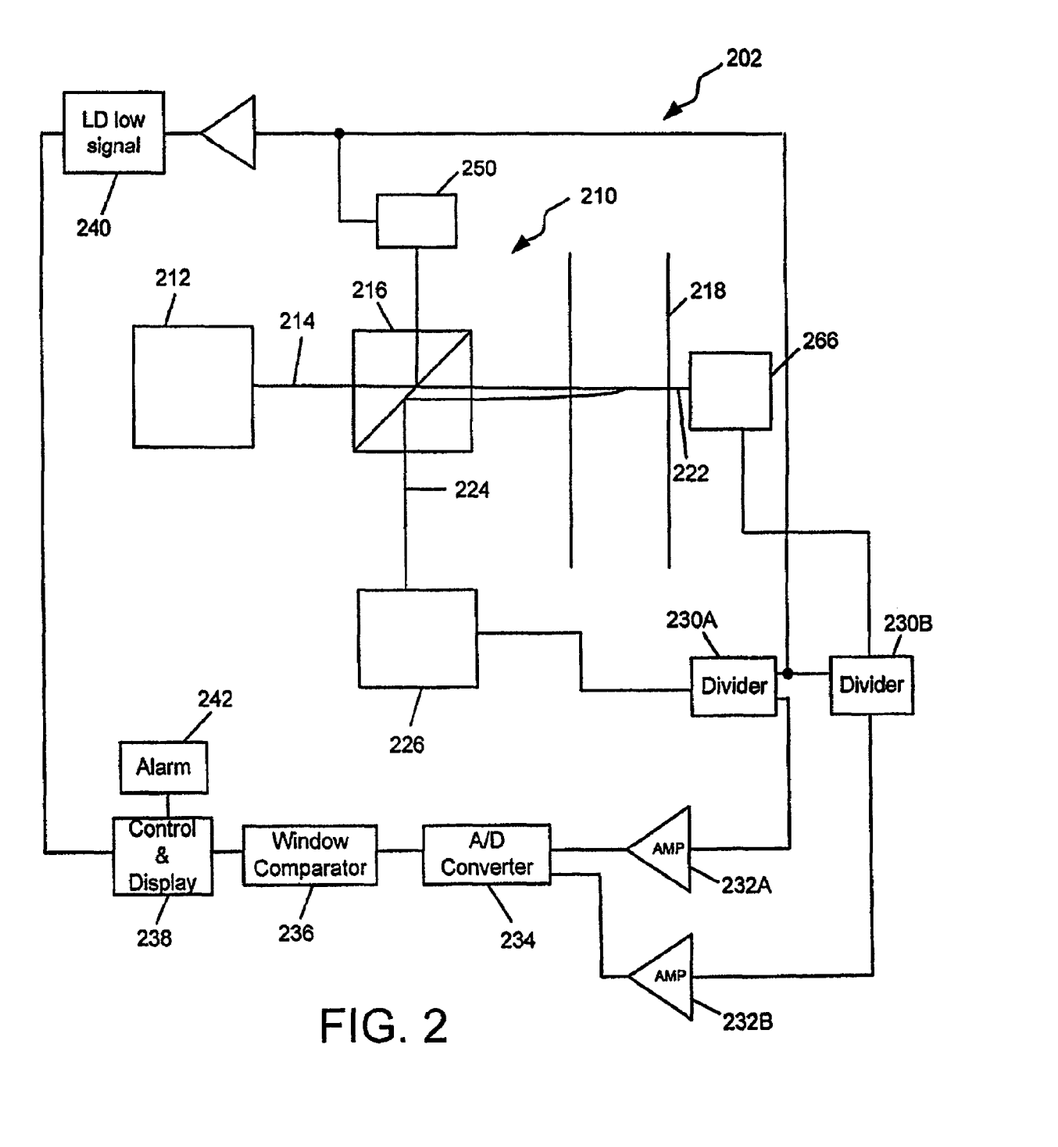
FIG. 2 is a block diagram of the particle detector system according to the first exemplary embodiment of the invention, incorporating the optical system of FIG. 1.

FIG. 2 is a block diagram of the particle detector system according to the first exemplary embodiment of the invention, incorporating the optical system 210 of FIG. 1. The optical system 210 includes the excitation source 212 directing the beam of electromagnetic radiation 214 into the first wavelength selective device 216. The beam of electromagnetic radiation 214 passes through the first wavelength selective device 216 into the medium 218 and a portion of the beam of electromagnetic radiation 214 is backward scattered to the first optical detector 226 and another portion of the beam of electromagnetic radiation 214 is forward scattered toward the particle detector 266.

Two signal dividers 230A, 230B divides an output of the first optical detector 226 and the particle detector 266, respectively, by the output of the power monitor detector 250. Two amplifiers 232A, 232B are connected to the output of the signal dividers 230A, 230B. An analog to digital converter 234 is connected to the amplifiers 232A, 232B. A window comparator circuit 236 is connected to the analog to digital converter 234. A control and output display unit 238 is connected to an output of the window comparator circuit 236. A low signal detection circuit 240 is connected to an output of the excitation source 212, which provides a power level related to the beam of electromagnetic radiation 214. The output of the low signal detection circuit 240 is also connected to the control and output display unit 238. An alarm device 242 is also connected to the control and output display unit 238. The control and output display unit 238 can be a computer or custom designed hardware/software to control operation of the particle detector.

Figure 3:
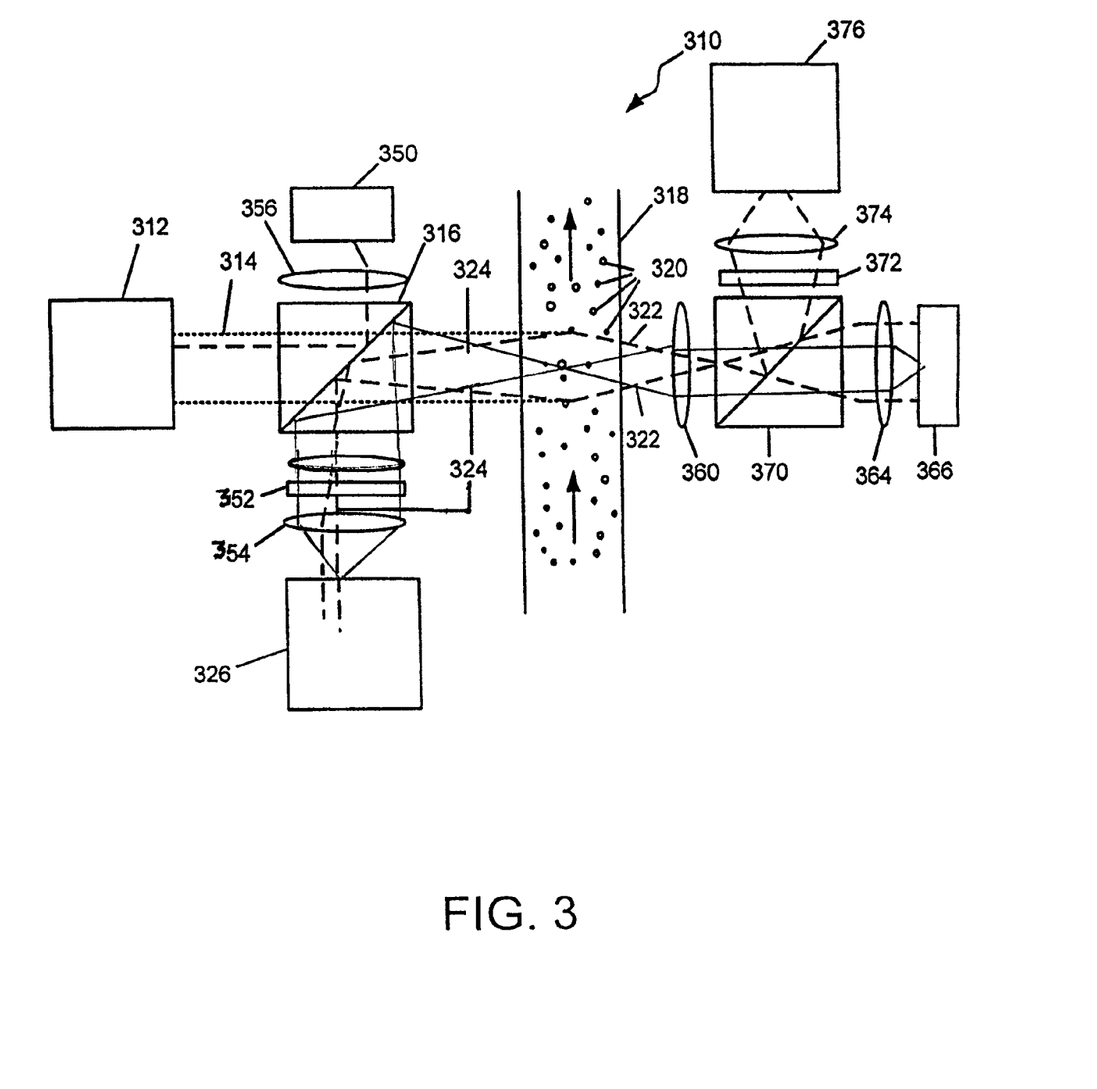
FIG. 3 is a representation of an optical system for a fluid particle detector system 701 According to a second exemplary embodiment of the invention.

FIG. 3 is a representation of an optical system for a fluid particle detector system according to a second exemplary embodiment of the invention. As shown in FIG. 3, the optical system 310 includes an excitation source 312 providing a beam of electromagnetic radiation 314 having a source wavelength. A first wavelength selective device 316 such as a dichroic beamsplitter is positioned to be impinged by the beam of electromagnetic radiation 314. The first wavelength selective device 316 is constructed to transmit at least a portion of any radiation having the source wavelength and to reflect radiation of other wavelengths. The first wavelength selective device 316 may operate to reflect potential spurious spectral emissions from the excitation source 312. A portion of the beam of electromagnetic radiation 314 may be reflected by the first wavelength selective device 316 toward a power monitor detector 350. The power monitor detector 350 may operate in communication with the excitation source 312 and, optionally, operate as a part of a feedback loop that maintains constant output power from the excitation source 312. The portion of the beam of electromagnetic radiation 314 reflected by the first wavelength selective device 316 toward the power monitor detector 350 may be focused by a power monitor lens 356.

A medium 318 containing particles 320 is positioned to be impinged by the beam of electromagnetic radiation 314. At least a portion of the beam of electromagnetic radiation 312 becomes scattered electromagnetic radiation within the medium 318. The scattered electromagnetic radiation includes forward scattered electromagnetic radiation 322 and backward scattered electromagnetic radiation 324. A first optical detector 326 is positioned to receive backward scattered electromagnetic radiation 324. The backward scattered electromagnetic radiation 324 may be reflected by the first wavelength selective device 316 toward the optical detector 326. A band pass filter 352 may be utilized between the first wavelength selective device 316 and the optical detector 326 to minimize any back scattered light from the beam of electromagnetic radiation 314 and/or to select out specific portions of the spectrum to be measured. A focusing lens 354 may be utilized between the first wavelength selective device 316 and the optical detector 326 to focus the backward scattered electromagnetic radiation 324 toward the optical detector 326.

As shown in FIG. 3, the forward scattered electromagnetic radiation 322 may be directed to impinge a first beam blocker lens 360. The first beam blocker lens 360 may be designed to reflect non-scattered elements of the beam of electromagnetic radiation 314, which may prevents glare on optical detectors. The forward scattered electromagnetic radiation may then be directed to an optic element 370, which is a second wavelength selective device 316 in the fourth exemplary embodiment. The first optic element 370 may allow passage of at least a portion of the forward scattered electromagnetic radiation 322 and reflect a portion of the forward scattered electromagnetic radiation 322. More specifically, the first optic element 370 may reflect a fluorescence signal portion of the forward scattered electromagnetic radiation 322, while allowing a remainder of the forward scattered electromagnetic radiation 322 to be transmitted through. A second beam blocker lens 364 may focus the transmitted portion of the forward scattered electromagnetic radiation 322 toward a particle detector 366. The particle detector 366 may, for instance, be a photodiode for sizing the particles 320.

The reflected fluorescence signal portion of the forward scattered electromagnetic radiation 322 may be directed toward a second optical detector 376. A second band pass filter 372 may be utilized between the first optic element 370 and the second optical detector 376 to minimize any back scattered light from the beam of electromagnetic radiation 314 and/or to select out specific portions of the spectrum to be measured. A focusing lens 374 may be utilized between the first optic element 370 and the second optical detector 376 to focus the reflected fluorescence signal portion of the forward scattered electromagnetic radiation 322 toward the second optical detector 376. The second optical detector 376 may, for instance, be a PMT optical detector.

Figure 4:
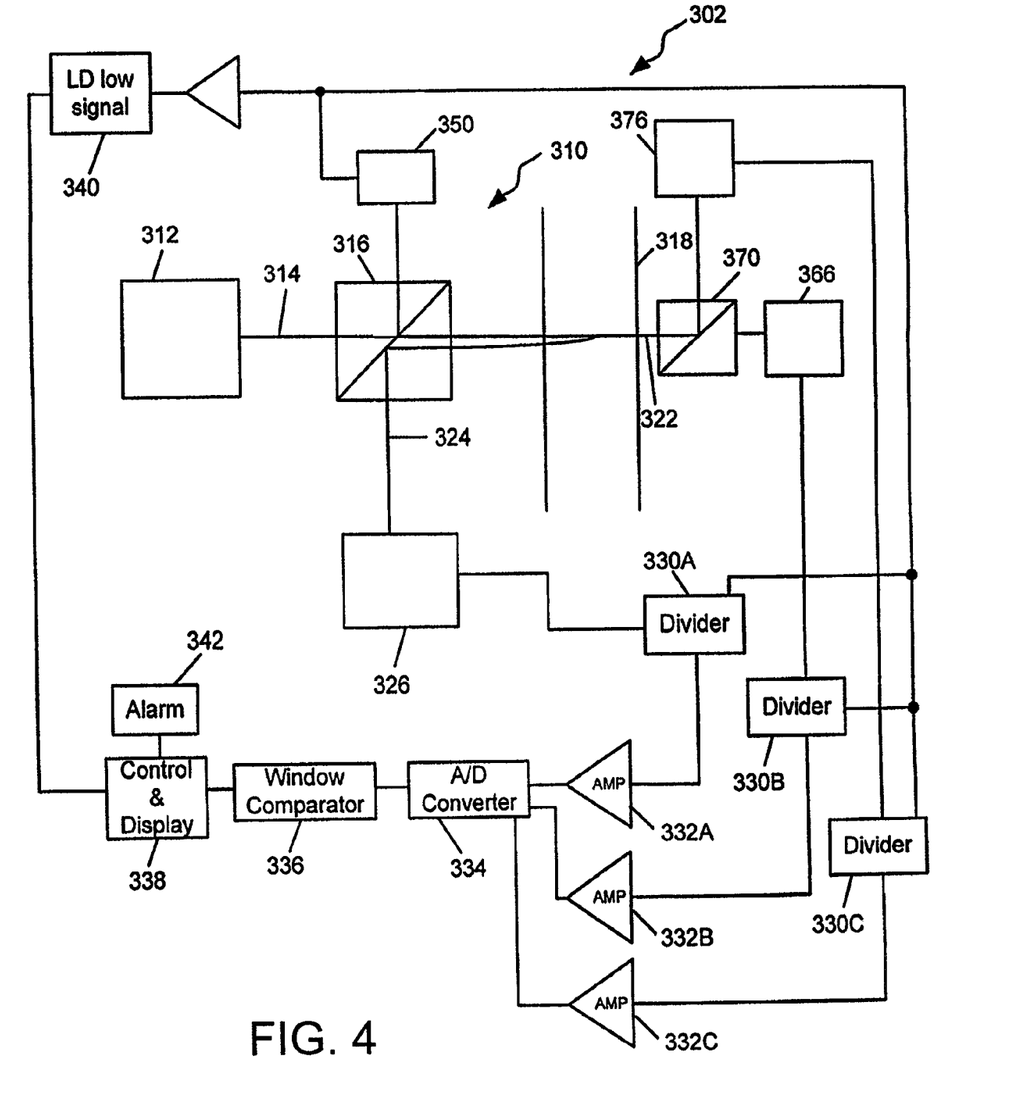
FIG. 4 is a block diagram of the particle detector system according to the second exemplary embodiment of the invention, incorporating the optical system of FIG. 3.

FIG. 4 is a block diagram of the particle detector system 301 according to the second exemplary embodiment of the invention, incorporating the optical system 310 of FIG. 3. The optical system 310 includes the excitation source 312 directing the beam of electromagnetic radiation 314 into the first wavelength selective device 316. The beam of electromagnetic radiation 314 passes through the first wavelength selective device 316 into the medium 318 and a portion of the beam of electromagnetic radiation 314 is backward scattered to the first optical detector 326 and another portion of the beam of electromagnetic radiation 314 is forward scattered toward the particle detector 366.

Three signal dividers 330A, 330B, 330C divide output of the first optical detector 326, the particle detector 366, and the second optical detector 376, respectively, by the output of the power monitor detector 350. Three amplifiers 332A, 332B, 332C are connected to the output of the signal dividers 330A, 330B, 330C. An analog to digital converter 334 is connected to the amplifiers 332A, 332B, 332C. A window comparator circuit 336 is connected to the analog to digital converter 334. A control and output display unit 338 is connected to an output of the window comparator circuit 336. A low signal detection circuit 340 is connected to an output of the excitation source 312, which provides a power level related to the beam of electromagnetic radiation 314. The output of the low signal detection circuit 340 is also connected to the control and output display unit 338. An alarm device 342 is also connected to the control and output display unit 338. The control and output display unit 338 can be a computer or custom designed hardware/software to control operation of the particle detector.

Figure 5:
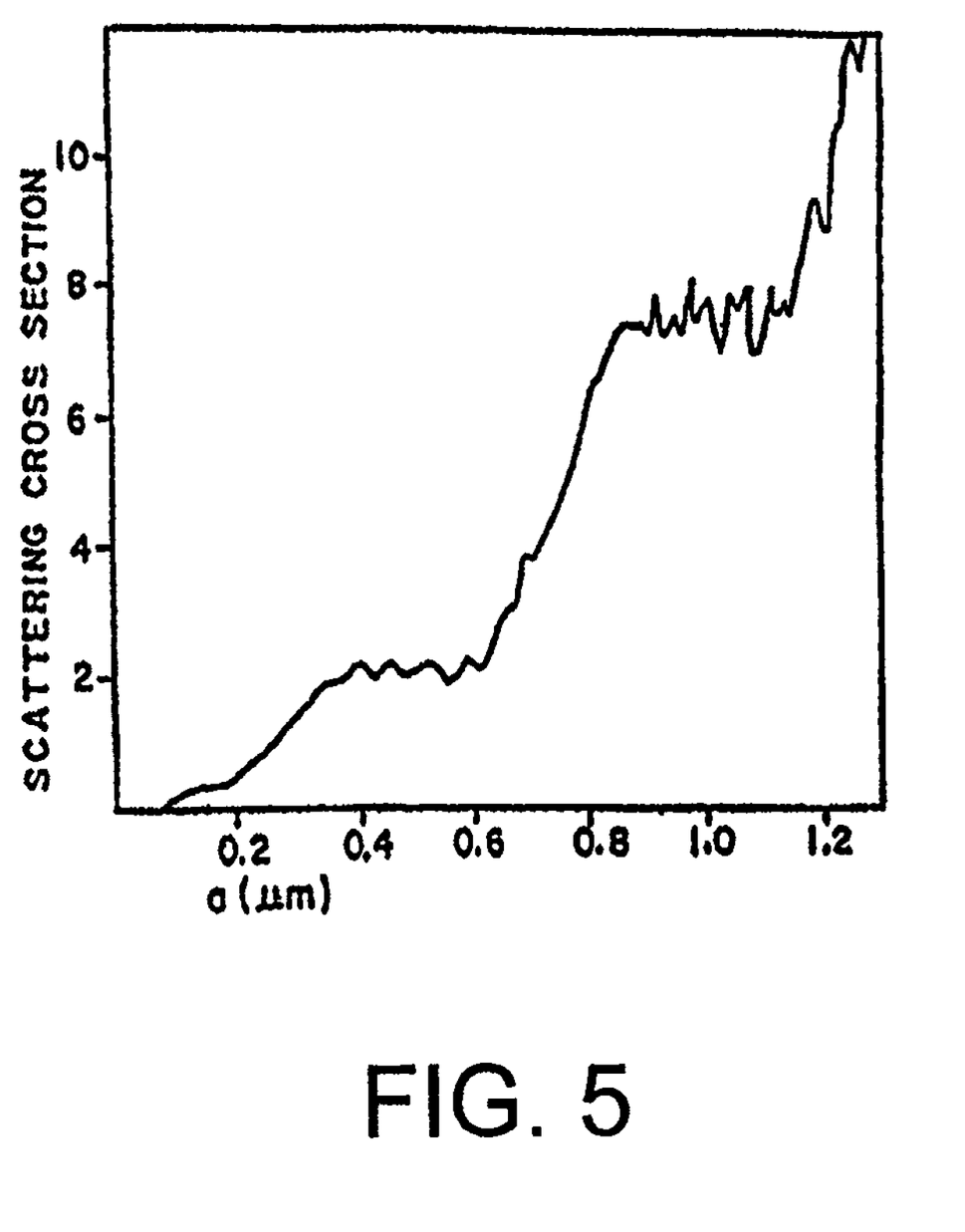
FIG. 5 is a graphic illustration of a relationship of Mie scattering cross-section to particle radius.

The system design is based upon the principle of Mie scattering of light by particles with sizes comparable with the wavelength of light. In the Mie scattering regime, both the angular distribution and the intensity of the scattered light are strongly dependent on particle size and shape. Scattering is characterized by the following properties: 1) the scattered light is concentrated in the forward and backward direction; 2) the angular distribution of the scattered light intensity is highly sensitive to the scattering particle size; and 3) the scattering cross-section of a particle is proportional to the particle size in a monotonic but complex manner. Using visible light, such as a visible laser diode light output beam of wavelength 0.67 µm, the Mie scattering method is ideally suited for detecting and characterizing fluid borne particles in the micron size range. FIG. 5 is a graphic illustration of a relationship of Mie scattering cross-section to particle radius.

The optical system 310 of the detector system 301, according to the second exemplary embodiment of the invention, uses the principle that scattering angle is proportional to particle size in order to eliminate light scattered outside a predetermined range using the first beam blocker lens 360 positioned in the path of light which has traveled through the sample. The particle detector 366 is designed to detect the particle size distribution in the sample by discriminating between pulses of different heights detected, since the scattering cross section of a particle is proportional to the particle size in a monotonic but complex manner, as described above and illustrated in FIG. 5. Therefore, the heights of the electrical pulses output from the particle detector 366 are dependent on the particle size.

Figure 6:
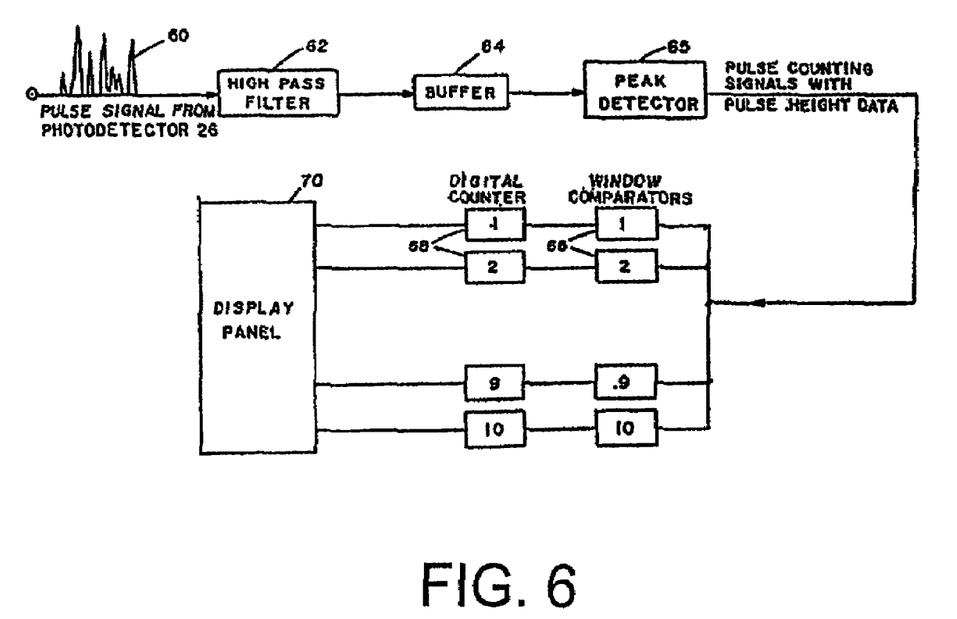
FIG. 6 is a block diagram of a pulse height measurement circuit, making up the analog to digital converter, the window comparator circuit, and the control and output display unit, in accordance with the second exemplary embodiment of the invention.
Figures 7, 7A:
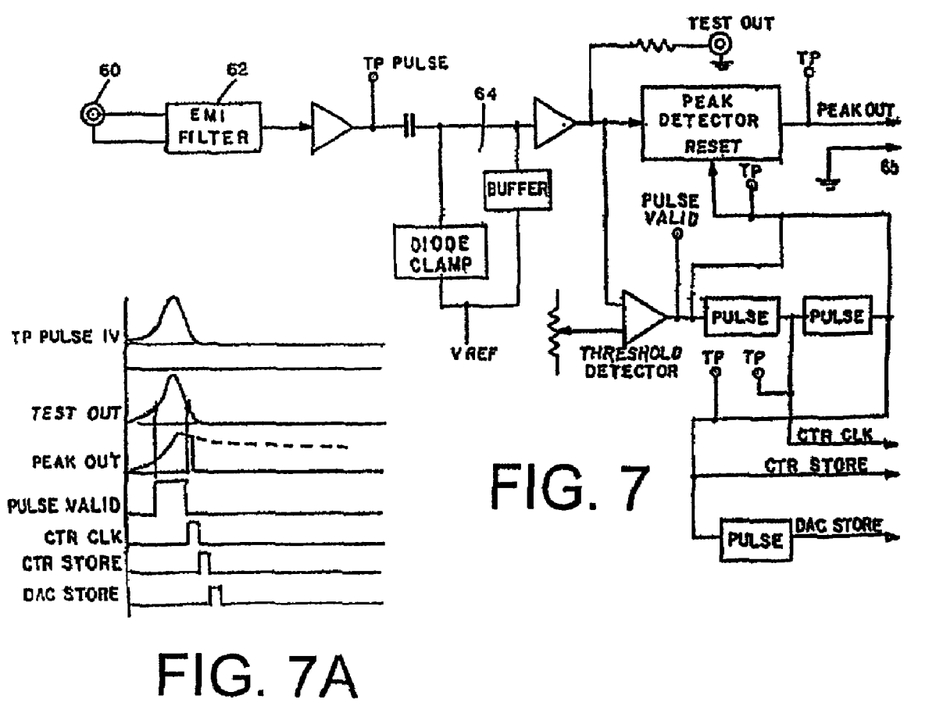
FIG. 7 is a schematic illustrating an analog to digital converter, in accordance with the second exemplary embodiment of the invention.
FIG. 7A is a graphic illustration of the outputs of the analog to digital converter at various points, in accordance with the second exemplary embodiment of the invention.

The output of the particle detector 366 is connected to one input of the second signal divider 330B, as indicated in FIG. 4, while the output of the power monitor detector 350 (which corresponds to the excitation source 312) is connected to the other input of the second signal divider 330B and the ratio of these signals is output from the second signal divider 330B. FIG. 6 is a block diagram of the pulse height measurement circuit, making up the analog to digital converter 334, the window comparator circuit 336, and the control and output display unit 338 in the second exemplary embodiment of the invention, while FIG. 7 is a schematic illustrating the analog to digital converter 334 in more detail. The output of the particle detector 366 will be a pulse signal, for example a signal 60 as illustrated in FIG. 6, of a series of analog pulses, with each pulse representing light scattered by a particle in the medium 318, and the height of the pulse being proportional to the particle size. Each incoming pulse from the particle detector 366 passes a high pass filter 62 in order to eliminate the DC background, and then goes through a buffer 64 to a peak detector 65 which will measure the height of the incoming pulse. The output of peak detector 65 will be a series of pulse counting signals with pulse height data. One example of the analog to digital converter 334 and peak detector circuit is illustrated in more detail in FIG. 7, with FIG. 7A illustrating pulse outputs at various points in the circuit. The output signal "PEAK OUT" in FIG. 7A is sent to the window comparator circuit 336 for classification. The other pulses illustrated in FIG. 7A are timing and enabling signals to tell the window comparator circuit 336 to take and store the count.

The window comparator circuit 336 has a series of window comparators 66 (labeled 1-10 in FIG. 6 by way of example) each designed to detect pulses in a predetermined voltage range (window voltage). Each window comparator 66 will send a signal to its associated digital counter 68 only if the incoming pulse height is within its window voltage (e.g. 5 mV to 7.5 mV for comparator #5). The outputs of the associated digital counters 68 are connected to a display panel 70, which will display particle numbers in each particle size, bin. Thus, the control and output display unit 338 may comprise a bar graph lit by light emitting diode (LED) arrays, with the LEDs being lit up in sequence for each particle size based on input from the associated counter, to produce a histogram of the particle size distribution. The bar graph may be in different colors for the different particle sizes. The outputs may also, or alternatively, be connected to a computer programmed to display a histogram of the particle size distribution on its display screen.

Figure 8:
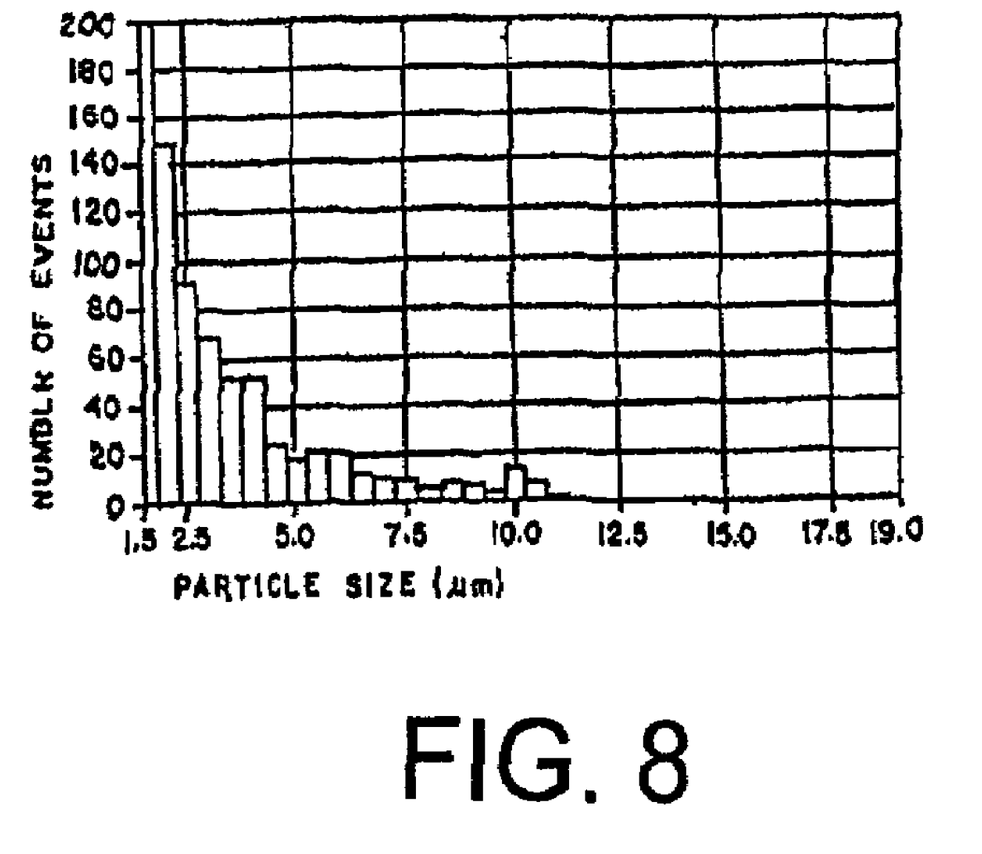
FIG. 8 illustrates an example of a histogram of particle size distribution.

The window comparator circuit 336 has a plurality of window comparators 66 and digital counters 68 for counting pulses corresponding to particle sizes in the range of interest. In FIG. 6, ten such bins are shown. However, fourteen bins may be provided for particle sizes from one to seven microns, at a 0.5 micron spacing. A smaller or greater number of comparators and counters may be provided if a smaller or larger size range is required, for example a more limited pathogen size range of 1 to 5 μm. FIG. 8 illustrates an example of a histogram of particle size distribution. Although this indicates a distribution in the range from 1 to 19 μm, it will be understood that the control and output display unit 338 may be programmed to display a particle size distribution histogram over the smaller range of 1-7 μm as discussed above or any desired range. The output of the control and output display unit 338 may also be connected to a visible and/or audible alarm device 342, such as an alarm light on the front of the housing and a buzzer or the like.

Any suitable software may be used to generate the output display histogram, such as LabView software available from National Instruments Corporation of Austin, Tex. This software may also be used to produce an output to activate the alarm device 342 if the number of counts in a size range corresponding to a pathogen or bio-agent particle size exceeds a predetermined level above the normal ambient level. This will help to reduce or even eliminate false alarms. The output of the computer may also be used to trigger a more elaborate bio-agent detection device, such as a PCR based anthrax detection apparatus. This combination detection scheme will be cost effective and will further reduce the risk of a false alarm.

In a modified arrangement of the invention, the histogram of the fluid borne particle size distribution may be compared to that of known weaponized bio-agents, since the processing procedure for such agents is known to have a signature size distribution unique to the machinery used in the process. Thus, the detector system of this invention can provide forensic information on the possible origin of the bio-agent manufacturer.

As noted above, the most probable bio-agents for use in a terrorist attack have size ranges from 1 μm to 7 μm. Table 1 below shows the characteristics of Category A bio-terrorist agents, as specified by the Center for Disease Control:

TABLE 1

| Category A bio-terrorist agent | |
| --- | --- |
| AGENT | SIZE CHARACTERISTICS |
| Bacillus Anthracis | Rod shape: width 1.0-1.2 μm, length 3.0-5.0 μm (spore 1.0 × 1.5 μm) |
| Yersinia pestis (plague) | Oval 1.0-2.0 μm |
| Clostidium botulinum | Rod shape: width 0.8-1.3 μm, length 4.4-8.6 μm |
| Francisella tularensis | Rod shape: width 0.2 μm, length 0.7 μm |

There exists in environmental air only a very small and constant concentration of naturally occurring fluid borne particles in the size range of about 1 μm to 7 μm. The particle size ranges of smog incursion in metropolitan areas and sudden growth of local dust source are peaked at 0.3 μm and 5 μm, respectively. Pollens and other allergens can also be present in the air during blooming seasons, and the size range of allergen particulates is from about 5 to 50 μm. Thus, few of these naturally occurring fluid borne particles are in the typical size range of weaponized bio-agents (1 to 7 μm). In addition, while mold may have a particle size of about 1 to 5 μm, the amount of mold particles in the air in any particular location generally does not vary suddenly. The detector system 301, according to the fourth exemplary embodiment, is therefore designed to detect particles in this specific size range and produce an output representing the range of particle sizes detected at 0.5 μm intervals. Any sudden and localized increase in the number of fluid borne particles within a 1 to 7 μm size range most likely signifies an intentional release of hostile bio-agents or pathogens. The system can be set up to detect and store a natural background level of particles within the size range of interest, and then use this as a comparison level for subsequent output histograms, in order to activate the alarm on detection of a sudden increase. The particle size distribution histogram of FIG. 8 indicates a probable hazardous situation where the number of particles detected in the size range of 1 to 7 μm is way over normal levels.

Although the particle detector system as above described will not identify the particular particle, it will serve as a sensitive and cost-effective warning of an fluid borne bio-agent attack because of the relative scarcity of fluid borne particles in the range of interest in normal meteorological conditions. Particles within this range can penetrate the human lungs and could be potentially harmful or even fatal for those inhaling them. The alarm device 342 provides a warning for individuals in the vicinity to evacuate the area immediately, reducing the exposure to such agents.

The detection system 301 also can be used to detect hazardous levels of potentially harmful dusts in manufacturing facilities. For example, harmful asbestos fibers are in the size range of about 5 μm, having a typical length of about 5 μm or longer and a diameter of about 1-2 μm. Beryllium dusts are also, harmful when breathed into the lungs, which will happen if they are in the 1-5 μm range. The detection system 301 could be provided in buildings containing asbestos, or when workers are working in such buildings, to provide a warning signal when an unusual spike in the 1 to 5 μm range is detected, which may indicate harmful levels of asbestos fibers in the air. Similarly, the detection system 301 may be used in the vicinity when workers are machining beryllium parts, in order to give a warning signal if the number of particles in the 1 to 5 μm size range suddenly increases, indicating the possible presence of harmful levels of beryllium dust. Even though the detection system 301 cannot differentiate asbestos or beryllium dusts from non-harmful particles in the same size range, any sudden increase in detected particle levels in this size range when working with asbestos or beryllium will provide an indication of a potentially hazardous situation requiring evacuation of the area and further testing.

Similarly, the detection system 301 also can be used in an asceptic manufacturing facility such as the food or pharmaceutical manufacturing facility such as manufacturer of drug or food processing facility to continuously monitor for microbial excursion so that remedial action may be taken as soon as possible. Also, the detection system 301 has been used as a continuous monitoring system to provide historical data and trending information which can alert facility managers in the event of microbial detection according to the specific clean room requirements of the facility.

In the detection system 301 described above, a two stage detection and discrimination process is used, with the optic system 310 of the system first eliminating light scattered outside a predetermined angular range incorporating the particle size range of interest. Subsequently, detected output pulses are discriminated according to pulse height, the number of pulses of each height are counted and converted to particle size within, e.g., 0.2 μm, and the results are displayed as a histogram, with a new histogram being generated at suitable time intervals to illustrate changing particle distribution conditions. However, instead of displaying a particle size distribution histogram, the optical portion of the detection system 301 may alternatively be arranged to direct only that part of the scattered light signal corresponding to a particle size range of 1 to 7 μm to the detector 14, and the remainder of the detection system 301 is then arranged to emit an alarm signal if the output of the detection system 301 exceeds a predetermined threshold level. This will provide a less accurate output, and does not provide any discrimination of particle sizes within the detected size range, but can still give a relatively accurate warning of the presence of an unusually large number of particles within a size range corresponding to known fluid borne pathogens allergens or other harmful particles, e.g., beryllium dust or asbestos. The optical system 301 of FIG. 3 would only have to be modified to provide a larger central blocking area to block light scattered by particles having a size greater than about 7 μm, and the output circuitry would be modified to provide a threshold level discriminator at the output of the particle detector 366, and to provide an output signal from the discriminator to activate an alarm if the detected signal is above the selected threshold.

The pathogen detector of this invention can be used in various applications. For example, it may be implemented as a battery powered, portable, hand-held detector for field personnel. In such case, an outer housing may hold both the optical unit as well as the electrical circuitry to count particles by size range, and will have a display of the current particle counts for each particle size, such as an LED display. It also may incorporate a transmitter for sending radio signals to a base station. It also may incorporate an audible alarm and a warning light for laser low power condition. A stand-alone, desktop version may also be provided for use in office buildings or the like. This will be similar to the field version, but will be powered from a standard electrical wall socket via an AC/DC converter. In the latter case, the detector may be used to provide protection from bio-agent contaminated letters or packages in office desktop settings.

The detector also may be part of a multiplexed system for building security, comprising a number of detectors in different rooms linked to a central monitoring computer or control station. The control station can be programmed to monitor the particle counts from each room, and to analyze the origin of any unusual increase in pathogen-size particles, and to predict the potential spread pattern within the building. The detectors may be hard wired, or may have radio transmitters for transmitting data to a central control station which again can analyze the origin of any detected increase in potential bio-agent particles, and the potentially spread of any bio-agent plume.

The fluid borne particle detector disclosed herein also advantageously may be used to monitor clean room facilities for potential contamination and/or material loss.

Utilizing a greater scope of the detector system 301, the alarm device 342 may be activated only after two conditions are met: (1) a sudden increase in the number of airborne particles within a predetermined size range (about 1 to about 7 nm) is detected; and (2) biological organisms or biological agents or organic materials are detected using, e.g., laser induced fluorescence as described below.

By themselves, particle size sensors are vulnerable to false alarms from ambient particulates. To further reduce these false alarms, the pathogen detector system 301 is a biological organism or biological agent verification detector combining the particle sizing capability with an UV light-induced fluorescence sensor to discriminate between biological and non-biological particles. The detector system 301 of the present invention includes the first optical detector 326 and the second optical detector 376 which includes a laser induced fluorescent sensor to detect metabolites which are present in biological organisms or biological agents, including biological warfare agents. More particularly, the optical system 310 includes an excitation source 312 operating in a wavelength of about 270 nm to about 410 nm, preferably about 350 nm to about 410 nm. A wavelength of about 270 nm to about 410 nm is chosen based on the premise that bio-agents comprise three primary metabolites: tryptophan, which normally fluoresces at about 270 nm with a range of about 220 nm-about 300 nm; nicotinamide adenine dinucleotide (NADH) which normally fluoresces at about 340 nm (range about 300 nm-about 400 nm); and riboflavin which normally fluoresces at about 400 nm (range about 320 nm-about 420 nm). Preferably, however, the excitation source 312 has a wavelength of about 350 to about 410 nm. This wavelength ensures excitation of two of the three aforesaid primary metabolites, NADH, and riboflavin in bio-agents, but excludes excitation of interference such as diesel engine exhaust and other inert particles such as dust or baby powder. Thus, in the fourth embodiment makes a judicial selection of wavelength range of the excitation source 312, which retains the ability of exciting fluorescence from NADH and riboflavin (foregoing the ability to excite tryptophan) while excluding the excitation of interferents such as diesel engine exhaust. This step is taken to reduce false alarms generated by diesel exhaust (which can be excited by short UV wavelengths such as 266 nm light).

Figure 9:
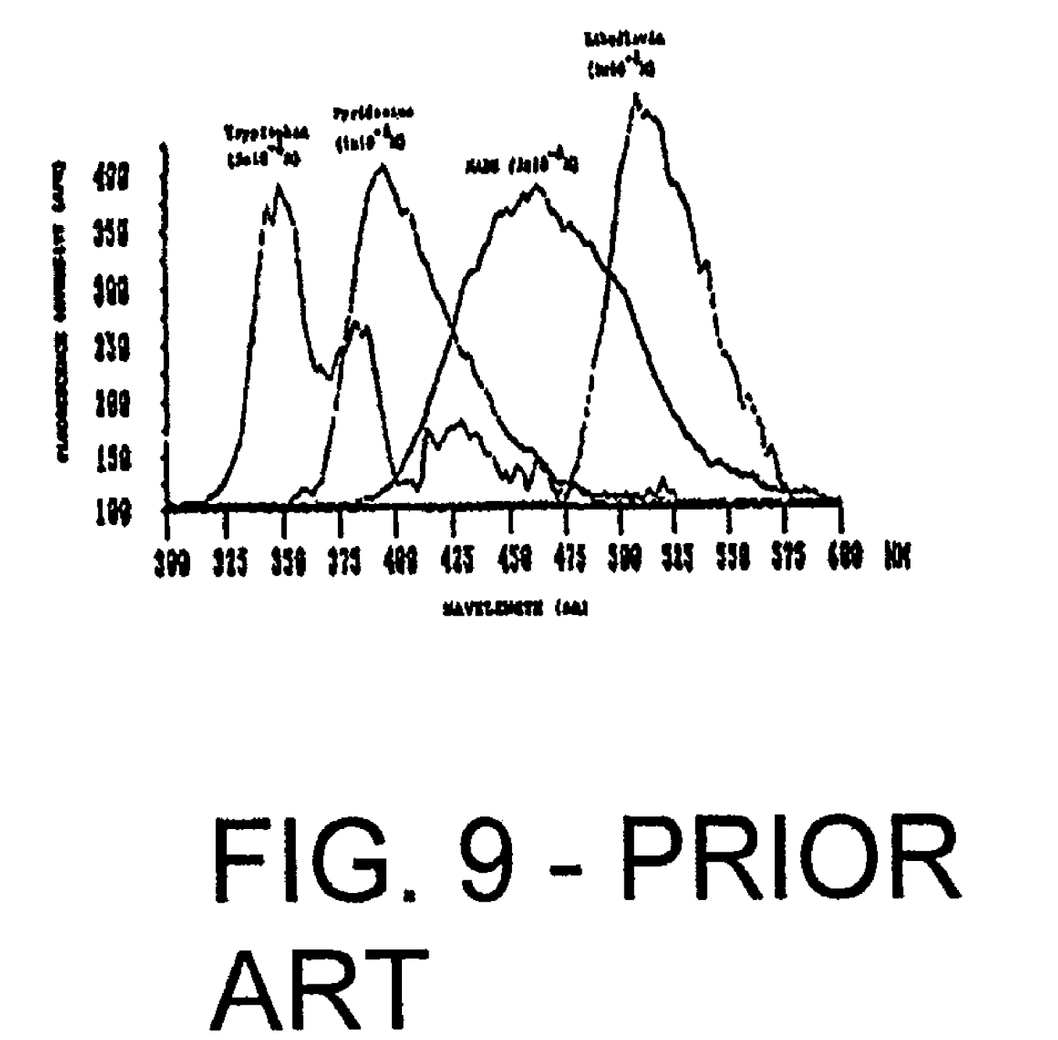
FIG. 9 shows the fluorescence emission spectra of four metabolites.

FIG. 9 shows the fluorescence emission spectra of aforementioned four metabolites. Spectral analyses, especially those with different excitation wavelength, will enable the probing of the composition of microbes and use the resultant information for the purpose of microbial detection and classification.

The output from the optical detectors 326, 376 is connected to the divider 330A, 330C, respectively, which in turn is connected via the amplifiers 330A, 330C and the analog to digital converter 334 to the control and display unit 338 which in turn is connected to the alarm device 342.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

The invention claimed is:

1. A particular detector system, comprising:
   a sampling area;
   a light source on one side of the sampling area for sending a substantially collimated beam of light through the sampling area;
   a beam blocking device on an opposite side of the sampling area having a non-transmissive region for blocking at least a portion of unscattered light emerging from the sampling area;
   a first optical detector positioned in the light path after the beam blocking device positioned to receive and detect a portion of forward scattered light scattered at various angles by particles of various sizes presence in the sampling area, and producing an output including information on a number and sizes of said particles;
   a second optical detector on the light source side of the sampling area positioned to receive and detect a portion of backward scattered light, and producing an output including information on a number of and fluorescence from said particles; and a first wavelength selective device positioned between the light source and the sampling area wherein backward scattered light emerging from within the sampling area is further directed by the first wavelength selective device to be received by the second optical detector.

2. The system of claim 1, further comprising an alarm unit for providing a warning signal if the number of particles detected within a predetermined size range exceeds a predetermined normal level within said predetermined size range.

3. The system of claim 1, wherein the light source emits light at a wavelength from about 270 nm to about 410 nm.

4. The system of claim 1, wherein the light source comprises a laser diode or a LED.

5. The system of claim 4, further comprising a collimator lens optically positioned between the light source and the first wavelength selective device.

6. The system of claim 1, further comprising a pulse height discriminator in communication with said first detector, a processing unit connected to an output of said pulse height discriminator for processing particle size distribution at a give time, based on the height of each pulse, producing a histogram of the airborne particle size distribution, and displaying the histogram on an output device.

7. A system of claim 1, further comprising:
a first optic element positioned after the beam blocking device and before the first detector to be impinged by at least a portion of the forward scattered light, wherein the first optic element transmits only a specific waveband of the portion of the forward scattered light to the first detector;
wherein the first optical element further directs a portion of the forward scattered light to the second optical detector positioned to receive and detect a portion of the forward scattered light directed by the first optic element, and
a filter positioned before the second detector;
whereby the second detector detects a fluorescence portion of the forward scattered light and produces an output including information on the fluorescence from said particle.

8. The system of claim 7, further comprising a first lens positioned to be impinged by the beam of light, wherein the first lens further comprises a collimating lens.

9. The system of claim 7, further comprising a power monitor detector lens positioned to receive and transmit radiation directed by the first wavelength selective device and a power monitor detector positioned to receive radiation from the power monitor detector lens, wherein the power monitor detector is in communication with the light source.

10. The system of claim 7, further comprising a third detector positioned after the sampling area, wherein the first optic element is positioned to direct at least a portion of the forward scattered light the third detector.

11. The system of claim 7, wherein the source wavelength is approximately between 350 nm and 410 nm and the first filter transmit light approximately below 400 nm.

12. The system of claim 7, further comprising a second beam blocker lens positioned optically between the first optic element and the first detector, wherein the second beam blocker lens transmits scattered light and absorbs non-scattered light.

13. The system of claim 1, further comprising at least one filter optically positioned between the sampling area and the first detector, wherein the filter transmits a portion of the forward scattered light from the sampling area and reflects a portion of the scattered light from the sampling area.

14. The system of claim 4, further comprising optical lens for shaping light from said light source into near collimated light.

15. The system of claim 1, wherein said light source includes optical lens for shaping light and/or removing noise from said light beam.

16. The system of claim 1, wherein the sampling area comprises an air sample.

17. The system of claim 1, wherein the sampling area comprises a water sample.

18. The system of claim 1, wherein the first wavelength selective device comprises a dichroic beamsplitter.

19. The system of claim 10, wherein the first optic element comprises a dichroic beamsplitter.

20. The system of claim 10, wherein the first optic element is a low pass filter.

21. A method of detecting pathogens and particles, the method comprising the steps of:
emitting a beam of light;
transmitting at least a portion of the beam of light through a first wavelength selective device;
impinging a sampling area containing particles with a portion of the beam of light, wherein the particles scatter the light in a forward direction and in a backward direction;
receiving at least a portion of the forward scattered light with a first optical detector, whereby particles are sized on the basis of the forward scattered light; and
receiving at least a portion of the backward scattered light at a second optical detector whereby fluorescence from the particles that scattered the light in the backward direction is detected and the particles are determined to be biologic or non-biologic on the basis of said fluorescence.

22. The method of claim 21, further comprising directing a portion of the forward scattered light toward a third optical detector using the first optic element, wherein the first optic element is a second wavelength selective device.

23. The method of claim 21, further comprising focusing a portion of the forward scattered light transmitted through the first optic element toward the first optical detector with a third lens, wherein the third lens absorbs non-scattered light.

24. The method of claim 21, further comprising focusing a portion of the backward scattered light directed by the first wavelength selective device toward the second optical detector with a fourth lens.

25. The method of claim 21, further comprising filtering a portion of the backward scattered light directed by the first wavelength selective device toward the second optical detector with a filter.

26. The method of claim 21, wherein the wavelength selective device is used to separate a fluorescence signal emitted from each individual particle from a light scatter signal.

27. The method of claim 26, wherein fluorescence intensity and size information of a particle collected by the system are used to determine whether the particle is biological or non-biologic.

28. A particle detector system, comprising:
a sampling area;
a light source on one side of the sampling area for sending a substantially collimated beam of light through the sampling area, whereby portions of the beam of light are scattered at various angles by particles of various sizes present in the sample area, and an unscattered portion of the beam of light remains unscattered;

a beam blocking device on an opposite side of the sampling area for blocking at least the portion of the unscattered portion of the beam of light and for limiting a range of particles measured;

a first optical detector positioned in the light path after the beam blocking device for detecting a portion of forward scattered light, and producing an output including information on a number of forward scattered particles in the light path within a predetermined size range;

a second optical detector on the light source side of the sampling area for detecting a portion of backward scattered light, and producing an output including information on the fluorescence of and a number of backward scattered particles in the light path within a predetermined size range; and a first optic element to transmit only a specific waveband of the portion of the forward scattered light toward the first optical detector, wherein other wavebands are reflected by the filter along an optic path toward the second optical detector.

29. The system of claim 28, wherein the light source emits light at a wavelength in the range from about 270 nm to about 410 nm.

30. The system of claim 28, wherein the light source comprises a laser diode or LED.

31. The system of claim 28, wherein the sampling area comprises an air flow through area.

32. The system of claim 28, wherein the sampling area comprises a water flow through.

* * * * *